United States Patent [19]

Peacock et al.

[11] Patent Number: 4,468,332
[45] Date of Patent: Aug. 28, 1984

[54] CONTROL OF LEGIONELLA PNEUMOPHILA IN WATER SYSTEMS

[75] Inventors: Jonathan H. B. Peacock, South Wirral; John B. Kurtz, Oxford, both of England

[73] Assignee: B.T.P. Cocker Chemicals Limited, London, England

[21] Appl. No.: 571,180

[22] Filed: Jan. 16, 1984

[30] Foreign Application Priority Data

Jan. 21, 1983 [GB] United Kingdom ............... 8301600

[51] Int. Cl.$^3$ .............................................. C02F 1/50
[52] U.S. Cl. ................................... 210/755; 210/764; 424/347; 422/37
[58] Field of Search ............... 210/755, 764, 765; 162/161; 424/335, 343, 345, 349, 353; 422/37

[56] References Cited

U.S. PATENT DOCUMENTS

| | | | |
|---|---|---|---|
| 3,852,471 | 12/1974 | Paulus et al. | 424/347 X |
| 3,989,585 | 11/1976 | Swered et al. | 210/764 X |
| 4,057,648 | 11/1977 | Hool et al. | 424/347 X |
| 4,111,844 | 9/1978 | Polony et al. | 424/347 X |
| 4,297,224 | 10/1981 | Macchiarolo et al. | 210/755 |

Primary Examiner—Thomas G. Wyse
Attorney, Agent, or Firm—Beveridge, DeGrandi & Kline

[57] ABSTRACT

A method of controlling the incidence and growth of the bacterium *Legionella pneumophila* in water systems of the recirculating type comprises adding to water in the water system a bactericidally effective amount of 2,2'-dihydroxy-5,5'-dichlorodiphenyl sulphide. At least one treatment agent selected from the group consisting of agents for dispersing organic matter, scale-formation inhibitors, corrosion inhibitors and anti-foaming agents can also be employed.

6 Claims, No Drawings

CONTROL OF LEGIONELLA PNEUMOPHILA IN WATER SYSTEMS

DESCRIPTION

The present invention relates to the treatment of water systems especially those of the recirculating type which utilize water for cooling purposes. The invention is concerned with the control of a specific Bacterium—Legionella pneumophila in such water systems.

Recirculating water systems used for cooling such as in air conditioning plant or industrial plant such as power stations has been shown to be a source of infection by the said bacterium present in the system. The infection arises from inhalation of the aerosol generated by the cooling towers of evaporation in such systems.

A biocide to be used in anti-microbial treatment of recirculating cooling water systems should be rapid in action, effective over a wide range of temperatures and pH and inexpensive. It must, of course be effective against the microbes in question if it is to be effective. It must also, however meet health and safety requirements and be acceptable to water authorities as suitable for discharge to waste. Furthermore it should have an acceptable odour and be free from foam- and scum- producing properties. Whilst there are many biocides, not all will meet the above requirements, and it is not a simple matter to find a biocide which is not only effective, but effective over long periods of time and which can be used continually and which also meet the above requirements.

A laboratory study of the effectiveness of biocides recommended for inhibiting biological growth in cooling towers and evaporative condensers of air-conditioning systems against Legionella pneumophila has been reported in Chemical Abstracts Vol. 94 No. 7, Feb. 16, 1981 page 102 No. 41943. In this study it was found that whilst chlorine, 2,2-dibromo-3-nitrilopropionamide and a compound containing didecyldimethyl-ammonium chloride and isopropanol were effective in destroying concentrations of $10^5$–$10^4$ viable cells per mL, other formulations consisting of 5-chloro-2-methyl-4-isothiazolin-3-one and 2-methyl-4-isothiazolin-3-one, disodium ethylene bis (thiocarbomate) and Na dimethyl dithiocarbomate, and a phenolic with Na pentachlor phenate, and sodium salts of other chlorophenols were less effective. It can thus be seen that there is no predictability in respect of the effectiveness of any given biocide against Legionella pneumophila even at laboratory level. Still less is there any predictability of the effectiveness of any given biocide in commercially operating water systems on a continuous basis.

It is an object of the present invention to provide an effective and inexpensive means for controlling the infestation of such water supplies by the said bacterium.

It has now been surprisingly found that the incorporation of 2,2'-dihydroxy-5,5' dichlorodiphenyl sulphide in a water system can effectively reduce the content of the said bacterium in said water to an acceptable level for a reasonable period and that regular dosages of the compound in bactericidally effective amounts has been found to effect satisfactory control of Legionella pneumophila in such water supplies.

According to the present invention a method of controlling the incidence and growth of the bacterium Legionella pneumophila in water systems of the recirculating type used in cooling systems is provided which comprises adding to the water in the water system a bactericidally effective amount of 2,2'-dihydroxy-5,5'-dichlorodiphenyl sulphide. The bactericide may be added separately but is preferably added with the usual treatment agents such as those added to disperse organic matter and to inhibit scale formation, corrosion and foaming.

The amount of bactericide added should be sufficient to reduce detectable bacteria to a level below 100 colony forming units (C.F.U.'s) per milliliter within a few hours of the addition. Thus as little as 10 ppm (on a weight basis) has been found to be effective after about 6 hours. About 25 ppm have been found effective after about 3 hours and 100 ppm after only 1 hour. Larger amounts may of course be used if desired, e.g. up to about 500 ppm. Preferably the amount added is from 25 to 200 ppm. The frequency of addition of the bactericide will depend on the amount added each time and the nature of the water system. In general a frequency of addition of once every 7 to 10 days produces satisfactory results with a concentration in the system of 25 to 200 ppm of the bactericide.

The activity of 2,2'-dihydroxy-5,5'dichlorodiphenyl sulphide was tested under laboratory conditions using L. Pneumophila serogroup I as the test organism. Yolk sacs of fertile hen eggs were inoculated with a freshly isolated strain (guinea pigs spleen suspension). The yolk sacs were incubated for 4 days and then harvested and stored at $-70°$ C. For the tests, buffered CYE medium was plated with harvested yolk sac material and incubated for 3–4 days at $37°$ C. After checking the bacterial growth obtained for purity, it was scraped off and suspended in sterile boiled water.

Test dilutions of the bacteriocide were made in 99 ml volumes of sterile boiled water to each of which was added 1 ml of the bacterial suspension with thorough mixing. 1 ml samples of the resulting mixture were drawn off, the first immediately after mixing and the remainder after 1, 3 and 6 hours respectively. Serial 10 fold dilutions of each sample were made and quantitative plate counts (Miles & Misra 1938) performed on phosphate or Aces buffered CYE medium. Colony counts were made after 4 days incubation. The results are tabulated below, each being the average of at least two tests:

| NUMBER OF C.F.U.s AFTER VARIOUS TIMES IN CONTACT WITH DILUTIONS OF BACTERICIDE | | | | |
|---|---|---|---|---|
| Bactericide | Time (hrs) | | | |
| conc. (ppm) | 0 | 1 | 3 | 6 |
| control | $5 \times 10^4$ | $5 \times 10^4$ | $7 \times 10^4$ | $3 \times 10^5$ |
| 100 | $2 \times 10^4$ | $< 10^2$ | $< 10^2$ | $< 10^2$ |
| 50 | $3 \times 10^4$ | $2 \times 10^3$ | $< 10^2$ | $< 10^2$ |
| 25 | $8 \times 10^5$ | $5 \times 10^4$ | $< 10^2$ | $< 10^2$ |
| control | $2 \times 10^7$ | $7 \times 10^5$ | $3 \times 10^4$ | $4 \times 10^4$ |
| 10 | $2 \times 10^7$ | $9 \times 10^5$ | $2 \times 10^3$ | |

We claim:
1. A method of controlling the incidence and growth of the bacterium Legionella pneumophila in water systems of the recirculating type which comprises adding to the water in said water system a bactericidally effective amount of 2,2'-dihydroxy-5,5'-dichloro diphenyl sulphide.

2. A method of controlling the incidence and growth of the bacterium Legionella Pneumophila in recirculating water systems utilized for cooling in air conditioning plants and cooling towers in industrial installations which comprises adding to the water in said water systems from 10 parts per million to 500 parts per million of 2,2'-dihydroxy-5,5'-dichloro diphenyl sulphide.

3. A method as claimed in claim 2, in which from 25 to 200 parts per million of 2,2'-dihydroxy-5,5'-dichloro diphenyl sulphide are added to the water system.

4. A method as claimed in claim 3, in which from 25 to 200 parts per million of 2,2'-dihydroxy-5,5'-dichloro diphenyl sulphide are repeatedly added to the water systems at intervals of from 7 to 10 days.

5. A method as claimed in claim 1, in which the water in the water system contains in addition to the bactericidally effective amount of 2,2'-dihydroxy-5,5'-dichloro diphenyl sulphide at least one treatment agent selected from the group consisting of agents for dispersing organic matter, scale-formation inhibitors, corrosion inhibitors and anti-foaming agents.

6. A method of controlling the incidence and growth of the bacterium Legionella pneumophila in water systems of the recirculating type which comprises repeatedly adding at intervals of from 7 to 10 days from 25 to 200 parts per million of 2,2'-dihydroxy-5,5'-dichloro diphenyl sulphide to the water in said water systems.

* * * * *